(12) United States Patent
Hong et al.

(10) Patent No.: US 9,342,887 B2
(45) Date of Patent: May 17, 2016

(54) HIGH ACCURACY IMAGE MATCHING APPARATUS AND HIGH ACCURACY IMAGE MATCHING METHOD USING A SKIN MARKER AND A FEATURE POINT IN A BODY

(71) Applicants: KOH YOUNG TECHNOLOGY INC., Seoul (KR); DAEGU GYEONGBUK INSTITUTE OF SCIENCE AND TECHNOLOGY, Daegu (KR)

(72) Inventors: Jaesung Hong, Daegu (KR); Jae-Yeong Park, Gyeongju-si (KR)

(73) Assignees: KOH YOUNG TECHNOLOGY INC., Seoul (KR); DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 0 days.

(21) Appl. No.: 14/345,215

(22) PCT Filed: Apr. 26, 2013

(86) PCT No.: PCT/KR2013/003647
§ 371 (c)(1),
(2) Date: Mar. 14, 2014

(87) PCT Pub. No.: WO2013/162332
PCT Pub. Date: Oct. 31, 2013

(65) Prior Publication Data
US 2015/0049907 A1 Feb. 19, 2015

(30) Foreign Application Priority Data

Apr. 27, 2012 (KR) .......................... 10-2012-0044917
Apr. 26, 2013 (KR) .......................... 10-2013-0046639

(51) Int. Cl.
*G06K 9/00* (2006.01)
*G06T 7/00* (2006.01)
(Continued)

(52) U.S. Cl.
CPC ............. *G06T 7/0044* (2013.01); *A61B 8/0833* (2013.01); *A61B 8/0858* (2013.01);
(Continued)

(58) Field of Classification Search
None
See application file for complete search history.

(56) References Cited

U.S. PATENT DOCUMENTS

| 7,346,199 B2 * | 3/2008 | Pfaff | ....................... G06T 19/00 382/128 |
| 2004/0034301 A1 * | 2/2004 | Falco | ............................ 600/427 |

(Continued)

FOREIGN PATENT DOCUMENTS

| JP | 2001-511691 | 8/2001 |
| KR | 10-2007-0004074 | 1/2007 |

(Continued)

OTHER PUBLICATIONS

Meeks et al, Optically Guided Patient Positioning Techniques, Seminars in Radiation Oncology vol. 15, Issue 3, Jul. 2005, pp. 192-201.*

(Continued)

*Primary Examiner* — Andrae S Allison
(74) *Attorney, Agent, or Firm* — Kile Park Reed & Houtteman PLLC

(57) ABSTRACT

A high accuracy image matching apparatus and a high accuracy image matching method using a skin marker and a feature point in a body, which uses ultrasonic probe or a radiation probe as a portion of the marker for image matching, are disclosed. As an embodiment, the high accuracy image matching apparatus and the high accuracy image matching method using a skin marker and a feature point in a body, use the ultrasonic probe or the radiation probe as a portion of marker for image matching indicating an anatomical feature point to reduce an error in operation point, and more precise operation can be possible and better operation result can be obtained by using the ultrasonic probe or a radiation probe.

6 Claims, 3 Drawing Sheets

(51) Int. Cl.
*A61B 8/00* (2006.01)
*A61B 19/00* (2006.01)
*A61B 8/08* (2006.01)
*G01S 15/89* (2006.01)

(52) U.S. Cl.
CPC .............. *A61B8/4245* (2013.01); *A61B 19/52* (2013.01); *A61B 8/4416* (2013.01); *A61B 8/5246* (2013.01); *A61B 2019/5255* (2013.01); *A61B 2019/5276* (2013.01); *A61B 2019/5289* (2013.01); *G01S 15/899* (2013.01); *G06T 2207/10132* (2013.01); *G06T 2207/30096* (2013.01); *G06T 2207/30204* (2013.01)

(56) References Cited

U.S. PATENT DOCUMENTS

| | | | |
|---|---|---|---|
| 2007/0073137 A1* | 3/2007 | Schoenefeld | 600/407 |
| 2007/0081709 A1* | 4/2007 | Warmath | G09B 23/285 382/128 |
| 2009/0018465 A1* | 1/2009 | Hessel et al. | 600/559 |
| 2010/0069720 A1* | 3/2010 | Fulghum et al. | 600/175 |
| 2010/0256504 A1* | 10/2010 | Moreau-Gaudry et al. | 600/476 |
| 2011/0021888 A1* | 1/2011 | Sing et al. | 600/302 |
| 2011/0112403 A1* | 5/2011 | Machtey et al. | 600/443 |
| 2011/0313288 A1* | 12/2011 | Chi Sing et al. | 600/437 |
| 2014/0257104 A1* | 9/2014 | Dunbar et al. | 600/443 |
| 2014/0309522 A1* | 10/2014 | Fullerton et al. | 600/424 |
| 2015/0011875 A1* | 1/2015 | Noordhoek et al. | 600/426 |
| 2015/0038832 A1* | 2/2015 | Bettenga | 600/424 |

FOREIGN PATENT DOCUMENTS

| | | |
|---|---|---|
| KR | 10-2007-0110965 | 11/2007 |
| KR | 10-2008-0034664 | 4/2008 |
| WO | 98/38919 | 9/1998 |

OTHER PUBLICATIONS

Szabó, Zoltán, and Adam Filipik. "Optical Tracking Systems for 3D Free-hand Ultrasound." Czech Science Foundation (CSF) (2005): 501-502.*

Lange Tl, Hünerbein M, Eulenstein S, Beller S, Schlag PM, Development of navigation systems for image-guided laparoscopic tumor resections in liver surgery, Recent Results Cancer Res. 2006;167:13-36.*

Written Opinion of the International Searching Authority for International Application No. PCT/KR2013/003647, dated Aug. 27, 2013.

International Search Report for International Application No. PCT/KR2013/003647 dated Aug. 27, 2013.

* cited by examiner

C: Camera (Polaris Spectra)
R: Reference marker of the patient
U: Ultrasound probe
p: target Point

HIGH ACCURACY IMAGE MATCHING APPARATUS AND HIGH ACCURACY IMAGE MATCHING METHOD USING A SKIN MARKER AND A FEATURE POINT IN A BODY

TECHNICAL FIELD

The present invention relates to a high accuracy image matching apparatus and a high accuracy image matching method using a skin marker and a feature point in a body, which uses ultrasonic probe or a radiation probe as a portion of the marker for image matching.

BACKGROUND ART

There exists an ultrasonic diagnostic apparatus capable of displaying an X-ray image or an MRI image together with ultrasonic image with the same cross section. According to the ultrasonic diagnostic apparatus, a position and an inclination of an ultrasonic probe are detected, and an X-ray image or an MRI image of a cross section corresponding to a detection position of a specified echo signal, based on detected information.

FIG. 1 is a diagram showing big error generated in a operation point when only skin marker is used in a conventional method. In image matching according to a conventional operational navigation, only a marker on a patient skin is used so that there exist big a target registration error (TRE) in an operation point in the body.

DETAILED DESCRIPTION OF THE INVENTION

Objects of the Invention

The present invention provides a high accuracy image matching apparatus and a high accuracy image matching method using a skin marker and a feature point in a body, which are capable of reducing error in an operation point by using an ultrasonic probe or a radiation probe as a portion of the marker.

Technical Solution

A high accuracy image matching apparatus using a skin marker and a feature point in a body for forming an embodiment, comprises a marker on a patient skin, indicating a first position regarding to a lesion in the patient body; a probe emitting ultrasonic wave or a radiation, and indicating a second position regarding the lesion; and a control part specifying a position of the lesion by calculating a crossing coordinates in which the first position and the second position coincide.

Additionally, a high accuracy image matching method using a skin marker and a feature point in a body for forming an embodiment, comprises indicating a first position of a lesion in a patient body through a marker on the patient skin; emitting ultrasonic wave or radiation through a probe to indicate a second position of the lesion; and specifying a position of the lesion by calculating crossing coordinates in which the first position and the second position coincide.

Advantageous Effects

According to embodiments of the present invention, an error may be reduced by using an ultrasonic probe or a radiation probe as a portion of the marker for image matching indicating anatomical feature point in a body.

Additionally, according to embodiments of the present invention, a precise operational navigation can be possible and better operation result can be obtained by using the ultrasonic probe or a radiation probe.

EMBODIMENTS OF THE INVENTION

Figure 1:
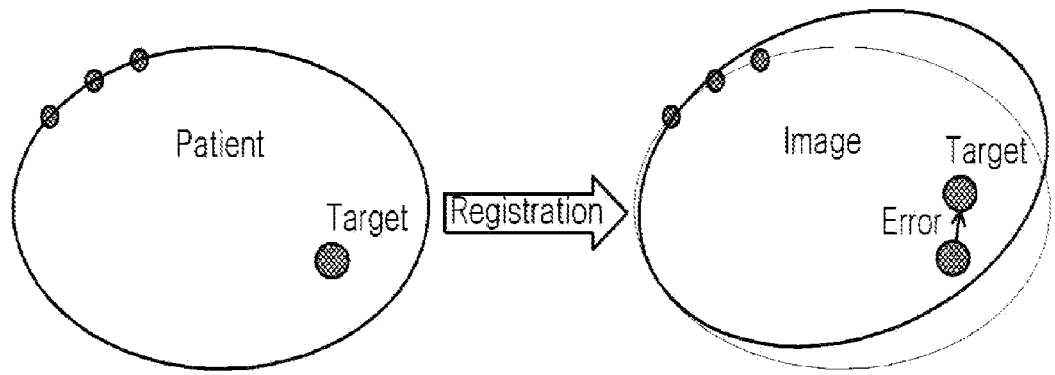
FIG. 1 is a diagram showing big error generated in a operation point when only skin marker is used in a conventional method.

Hereinafter, preferred embodiments of the present invention will be explained referring to figures. However, the present invention is not limited to the embodiments. Same reference numerals in figures corresponds to same elements.

On the other hand, in embodiments of the present invention, an ultrasonic wave based image matching apparatus will be explained, but CT using X-ray a radiographic image may be used as a substitute of as ultrasonic image. Additionally, the present invention may be applied to an image capturing and detecting device capable of measuring a shape of position of a specific point in a body by using wave of a specific wavelength and magnetic wave.

Figure 2:
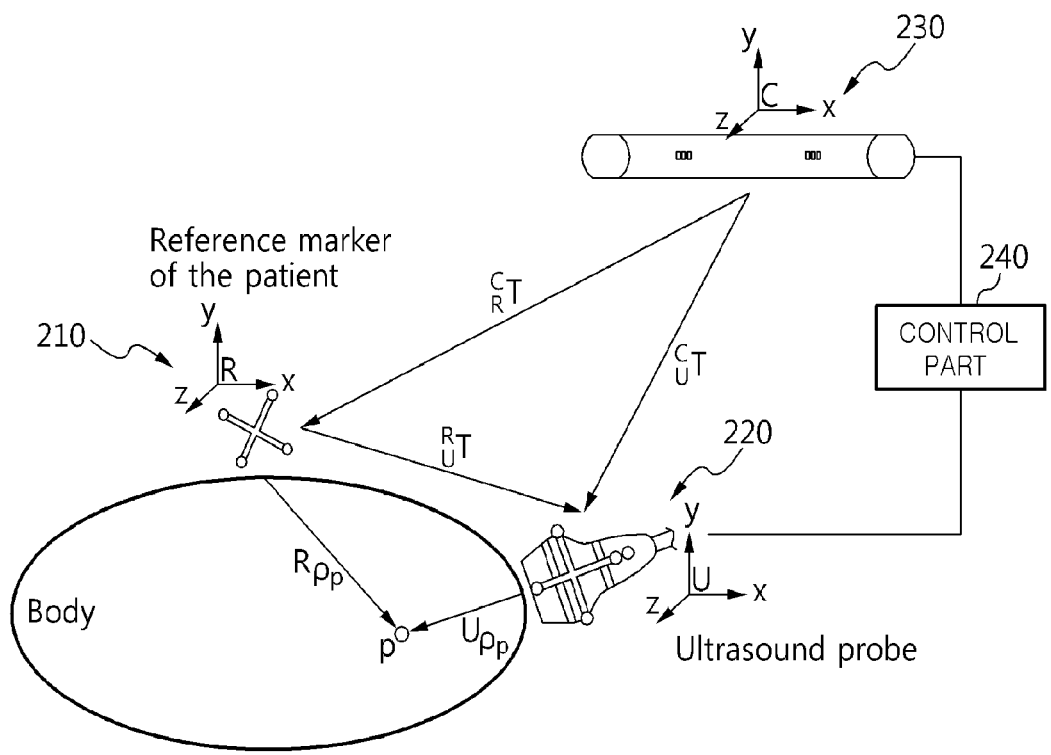
FIG. 2 is a diagram showing a high accuracy image matching apparatus using a skin marker and a feature point in a body, which is capable of enhancing accuracy by using an anatomical feature point in a body as the skin marker according to an embodiment of the present invention.

FIG. 2 is a diagram showing a high accuracy image matching apparatus using a skin marker and a feature point in a body, which is capable of enhancing accuracy by using an anatomical feature point in a body as the skin marker according to an embodiment of the present invention.

Referring to FIG. 2, a high accuracy image matching apparatus may include a marker 210, an ultrasonic probe (or a radiographic image probe) 220, a camera 230, a control part 240, etc.

The marker 210 is positioned on a patient body to indicate a first position regarding a lesion in the patient body through an extension line passing through a center thereof.

The ultrasonic probe 220 obtains a position, a shape and a feature of a target. The ultrasonic probe 220 emits ultrasonic wave with directivity to indicate a second position regarding lesion in the patient body. Alternatively, when a radiographic image probe is used as a substitute of the ultrasonic probe 220, a radiation with directivity and amount that is harmless to a human body may be emitted to indicate the second position.

The control part 240 calculates a feature point corresponding to the position of the lesion by calculating a crossing coordinate corresponding to a coincidence point of the first position indicated by the marker 210 and the second position in the patient body, which is indicated by the ultrasonic probe 220.

The camera 230 captures the marker 210 and the ultrasonic probe 220.

The control part 240 measures a distance $^C_RT$ between the camera 230 and the marker 210 and a distance $^C_UT$ between the camera 230 and the ultrasonic probe 220, based on the image captured by the camera 230, and calculates a distance $^R_UT$ between the marker 210 and the ultrasonic probe 220 through a calculation $^C_RT^{-1}*^C_UT$ having parameters of the distance $^C_RT$ and the distance $^C_UT$.

The control part 240 calculates the distance between the marker 210 and the ultrasonic probe 220, and calculates a position in which extension lines passing through the first and second positions coincides as the crossing coordinate. The control part 240 calculates a coordinate of the feature point indicated by the marker 210 and the ultrasonic probe 220 through a triangulation.

The control part 240 calculates the coordinates of the feature point determined by the extension line indicated by the marker 210 and the extension line indicated by the ultrasonic probe 220.

Referring to FIG. 2, an example for calculating real P will be explained as follows.

The control part 240 measures the distance $^C_RT$ between the camera 230 and the marker 210, and the distance $^C_UT$ between the camera 230 and the ultrasonic probe 220.

The control part 240 calculates a distance $^R_UT$ between the marker 210 and the ultrasonic probe 220 through a calculation $^C_RT^{-1}*^C_UT$ having parameters of the distance $^C_RT$ and the distance $^C_UT$.

The control part 240 measures a contained angle Q between an imaginary line connecting the marker 210 and the ultrasonic probe 220 and the extension line passing through the second position.

The control part 240 calculates a distance $^U_PP$ between the ultrasonic probe 220 and the second position through a calculation $^R_UT*COS\ Q$ having parameters of the distance $^R_UT$ and the contained angle Q.

The control part 240 calculates a distance $^R_PP$ between the marker 210 and the first position through a calculation $^R_UT*^U_PP$ having parameters of the distance $^R_UT$ and the distance $^U_PP$.

The control part 240 calculates a feature point P spaced apart from the marker 210 by the distance $^R_PP$ as the crossing coordinate. For example, supposing the position of the marker 210 to be null, the control part 240 may indicates the position spaced apart from the marker 210 by the distance $^R_PP$ as the feature point P. In this case, the feature point P may be expressed by (p, q, r) in a three dimensional coordinate.

According to other embodiment, a stereo camera captures an image of the marker 210 and the ultrasonic probe 220.

The control part 240 calculates distances from the marker 210 and the ultrasonic probe 220, respectively and a contained angle between the two devices 210 and 220, and calculates the distance between the marker 210 and the ultrasonic probe 220 by using the distances and the contained angle.

The control part 240 calculates the coordinate of the feature point P indicated by the marker 210 and the ultrasonic probe 220 by using the distance T between the marker 210 and the ultrasonic probe 220.

The control part 240 calculates a contained angle between the distance T and an extension line R passing through the first position, and a contained angle between the distance T and an extension line U passing through the second position.

The control part 240 calculates the coordinate of the feature point P indicated by the marker 210 and the ultrasonic probe 220 through a triangulation by using the distance T and two contained angles.

Figure 3:
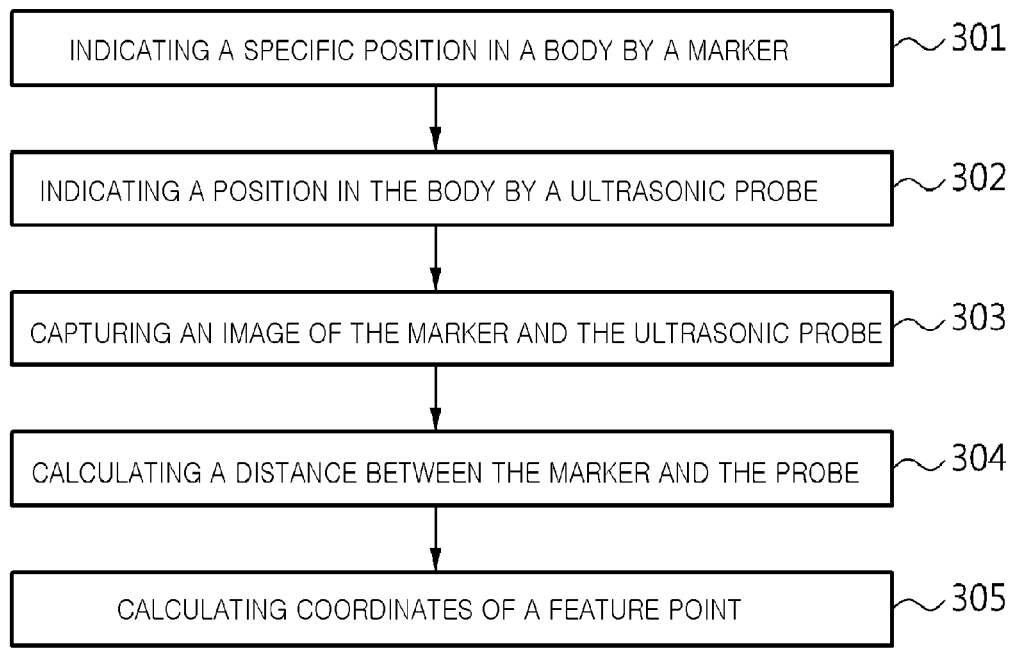
FIG. 3 is a flow chart showing a high accuracy image matching method using a skin marker and a feature point in a body according to an embodiment of the present invention.

FIG. 3 is a flow chart showing a high accuracy image matching method using a skin marker and a feature point in a body according to an embodiment of the present invention.

Referring to FIG. 3, an operation of the high accuracy image matching apparatus for calculating the feature point will be explained.

The high accuracy image matching apparatus indicates the first position of a lesion in a patient body through a marker on the patient skin (301).

The high accuracy image matching apparatus controls the ultrasonic probe to emit ultrasonic wave to indicate the second position of the lesion in the patient body (302).

The high accuracy image matching apparatus captures images of the marker and the ultrasonic probe by using the camera (303).

The high accuracy image matching apparatus measures the distance $^C_RT$ between the camera and the marker and the distance $^C_UT$ between the camera and the ultrasonic probe, and calculates the distance $^R_UT$ between the marker and the ultrasonic probe through a calculation $^C_RT^{-1}*^C_UT$ having parameters of the distance $^C_RT$ and the distance $^C_UT$ (304).

The high accuracy image matching apparatus calculates the distance between the marker and the ultrasonic probe, and calculates the position in which an extension line passing through the first position and an extension line passing through the second position as the crossing coordinate. The high accuracy image matching apparatus calculates the coordinate of the feature point indicated by the marker and the ultrasonic probe through triangulation.

The high accuracy image matching apparatus calculates the coordinates of the feature point determined by an extension line indicated by the marker and an extension line indicated by the ultrasonic probe (305).

Figure 4:
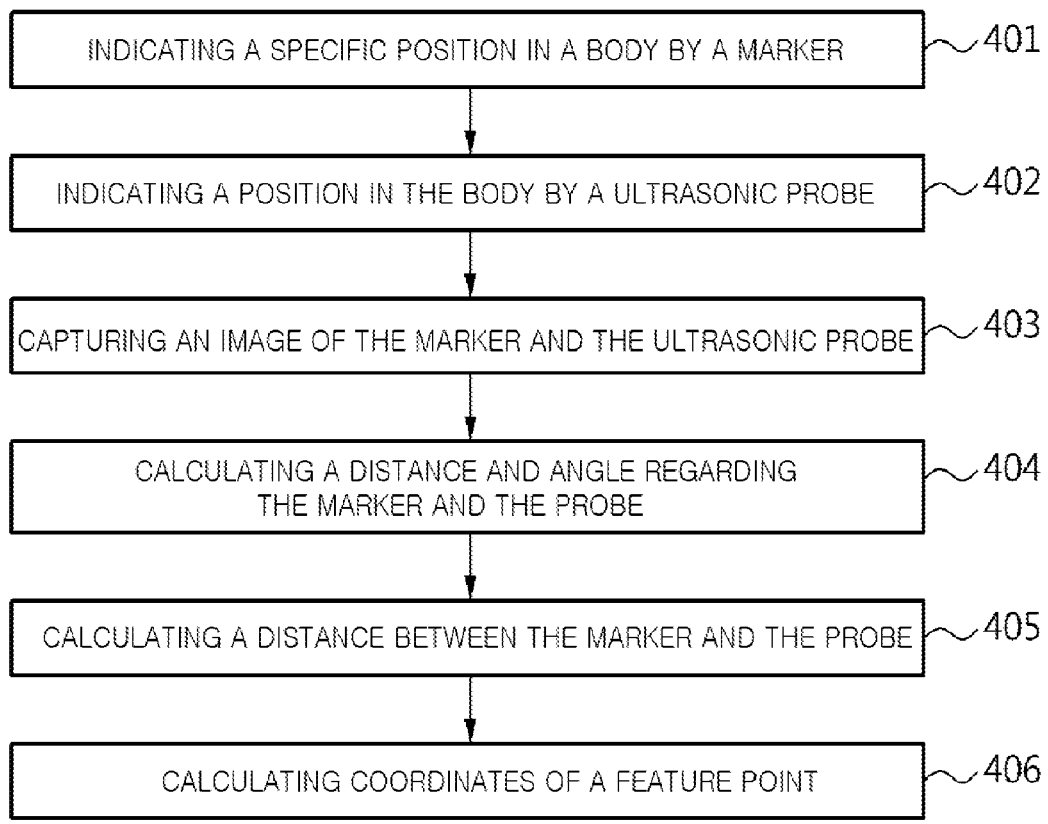
FIG. 4 is a flow chart showing a high accuracy image matching method using a skin marker and a feature point in a body according to another embodiment of the present invention.

FIG. 4 is a flow chart showing a high accuracy image matching method using a skin marker and a feature point in a body according to another embodiment of the present invention.

Referring to FIG. 4, an operation of the high accuracy image matching apparatus for calculating the feature point will be explained.

The high accuracy image matching apparatus indicates the first position of a lesion in a patient body through a marker on the patient skin (401).

The high accuracy image matching apparatus controls the ultrasonic probe to emit ultrasonic wave to indicate the second position of the lesion in the patient body (402).

The high accuracy image matching apparatus captures images of the marker and the ultrasonic probe by using the camera (403).

The high accuracy image matching apparatus calculates distances from the marker and the ultrasonic probes respectively, and a contained angle between two devices (404), and the high accuracy image matching apparatus calculates the distance between the marker and the ultrasonic probe by using the contained angle (405).

The high accuracy image matching apparatus calculates a coordinate of the feature point P indicated by the marker and the ultrasonic probe by using the distance T between the marker and the ultrasonic probe (406).

The high accuracy image matching apparatus calculates a contained angle between the distance T and an extension line R passing through the first position, and a contained angle between the distance T and an extension line U passing through the second position.

The high accuracy image matching apparatus calculates the coordinate of the feature point P indicated by the marker 210 and the ultrasonic probe 220 through a triangulation by using the distance T and two contained angles. That is, in summary, the high accuracy image matching apparatus calculates the featuring point by using the first position in a body, which is indicated by the marker and the second position in the body, which indicated by the ultrasonic probe. The high accuracy image matching apparatus calculates the feature point determined by the extension line indicated by the marker and the extension line indicated by the ultrasonic probe.

The operational navigation is required for an exact and safe operation and has become widely used. In the operational navigation, error may be generated during image capturing and matching process. In operation requiring high accuracy, such as an otorhinolaryngology field or a neurosurgery field, such an error may significantly influences the operation result. The present invention reduces the error in image matching so that more exact operational navigation can be performed and better operation may be performed.

The apparatus described above may be embodied through a hardware component, a software component, and/or a combination of the hardware component and the software component. For example, the apparatus and elements described in the embodiments, may be embodied through at least one wide use computer or special purpose computer such as a processor, a controller, an arithmetic logic unit (ALU), a digital signal processor, a microcomputer, a field programmable array (FPA), a programmable logic unit (PLU), a microprocessor, an any other device capable of performing an instruction and responding. The processor may perform at least one operating system (OS) and software application performed on the OS. Further, the processor may access, store, handle, process and generate data. For convenience understanding, the processor is embodied only one, but the processor may be embodied by a plurality of processors or a plurality types of processors as a person skilled in the art may easily understand. For example, the processor may include a plurality of processor or one processor and one controller. Further, other processing configuration such as a parallel processor may be possible.

The software may include a computer program, a code, an instruction, or a combination thereof, construct the processor as required, and order to the processor to perform independently and in combination. The software and/or data may be translated by the processor or be embodied permanently or temporarily to some types of machine, component, physical device, virtual equipment, computer storage or device, or transmitting signal wave for providing order or data to the processor. The software may be distributed in a computer systems connected by networks to that the software may be stored and performed in a distributed method. The software and data may be stored in at least one of computer readable medium.

The method according to the embodiments may be embodied through program orders performed by various computer means to be stored in the computer readable medium. The computer readable medium may include a program, a data file, a data structure and a combination thereof. The program order may be constructed specially for performing the embodiments or well known to a person in a computer software technology. The computer readable medium include for example a magnetic medium such as a hard disk, a floppy disk and magnetic tape, an optical medium such as CD-ROM and DVD, a magneto-optical medium such as floptical disk, and a specially performed device for storing and performing program order such as ROM, RAM and flash memory. The program order includes not only a machine language generated by a compiler but also high-level language that can be performed by a computer through a interpreter. The hardware device may be formed by at least one software module for performing the embodiments, and vice versa.

As described above, the detailed description of the present invention is described with regard to the preferable embodiment and figure of the present invention, however, a person skilled in the art may amend or modify the present invention within the spirit or scope in the following claim of the present invention. For example, the explained technic may be performed differently in order, and/or embodiments such as system, a structure, a device, a circuit, etc. may be assembled, combined or substituted by an element with same function.

Therefore, other realization or other embodiments, and equivalent with the claims belong to the claim.

What is claimed is:

1. A high accuracy image matching apparatus using a skin marker and a feature point in a body, comprising:
   a marker on a patient skin, indicating a first position regarding to a lesion in the patient body;
   a probe emitting ultrasonic wave or a radiation, and indicating a second position regarding the lesion;
   a camera capturing an image of the marker and the probe; and
   a control part specifying a position of the lesion by calculating a distance $^R_U T$ between the marker and the probe and crossing coordinates in which the first position and the second position coincide,
   wherein the control part measures a distance $^C_R T$ between the camera and the marker, and a distance $^C_U T$ between the camera and the probe, and
   calculates the distance $^R_U T$ between the marker and the probe through a calculation $^C_R T^{-1} *^C_U T$ having parameters of the distance $^C_R T$ and the distance $^C_U T$.

2. The high accuracy image matching apparatus using a skin marker and a feature point in a body of claim 1, wherein the control part calculates a position in which an extension line passing through the first position and an extension line passing through the second position coincide as the crossing coordinate.

3. The high accuracy image matching apparatus using a skin marker and a feature point in a body of claim 1, wherein the control part measures a contained angle Q between an imaginary line connecting the marker and the probe and an extension line passing through the second position,
   calculates a distance $^U_P P$ between the probe and the second position through a calculation $^R_U T * COS\ Q$ having parameters of the distance $^R_U T$ and the contained angle Q,
   calculates a distance $^R_P P$ between the marker and the first position through a calculation $^R_U T *^U_P P$ having parameters of the distance $^R_U T$ and the distance $^R_P P$, and
   calculates a feature point P spaced apart from the marker by the distance $^R_P P$ as the crossing coordinate.

4. A high accuracy image matching method using a skin marker and a feature point in a body, comprising:
   indicating a first position of a lesion in a patient body through a marker on the patient skin;
   emitting ultrasonic wave or radiation through a probe to indicate a second position of the lesion;
   capturing an image of the marker and the probe by a camera; and
   specifying a position of the lesion by calculating a distance $^R_U T$ between the marker and the probe and crossing coordinates in which the first position and the second position coincide,
   wherein the high accuracy image matching method further comprises:

measuring a distance $^C_RT$ between the camera and the marker, and a distance $^C_UT$ between the camera and the probe, and calculating the distance $^R_UT$ between the marker and the probe through a calculation $^C_RT^{-1} * {^C_UT}$ having parameters of the distance $^C_RT$ and the distance $^C_UT$.

5. The high accuracy image matching method using a skin marker and a feature point in a body of claim 4, wherein calculating crossing coordinates includes calculating a position in which an extension line passing through the first position and an extension line passing through the second position coincide as the crossing coordinate.

6. The high accuracy image matching method using a skin marker and a feature point in a body of claim 4, wherein calculating the crossing coordinates comprising:

measuring a contained angle Q between an imaginary line connecting the marker and the probe and an extension line passing through the second position;

calculating a distance $^U_PP$ between the probe and the second position through a calculation $^R_UT * \cos Q$ having parameters of the distance $^R_UT$ and the contained angle Q, calculating a distance $^R_PP$ between the marker and the first position through a calculation $^R_UT * {^U_PP}$ having parameters of the distance $^R_UT$ and the distance $^U_PP$, and calculating a feature point P spaced apart from the marker by the distance $^R_PP$ as the crossing coordinate.

\* \* \* \* \*